United States Patent [19]

Jaquith

[11] Patent Number: 5,624,403
[45] Date of Patent: Apr. 29, 1997

[54] MANAGEMENT SYSTEM FOR MEDICAL TUBES AND CABLES

[76] Inventor: Jerrie L. Jaquith, 23030 SW. Jaquith Rd., Newberg, Oreg. 97132

[21] Appl. No.: 454,089

[22] Filed: May 30, 1995

[51] Int. Cl.⁶ .................................................. A61M 25/00
[52] U.S. Cl. .................. 604/179; 604/180; 128/DIG. 26
[58] Field of Search .................................. 604/174, 179, 604/180; 128/DIG. 15, DIG. 26

[56] References Cited

U.S. PATENT DOCUMENTS

| | | | |
|---|---|---|---|
| 3,782,382 | 1/1974 | Naftulin et al. | |
| 4,029,103 | 6/1977 | McConnell. | |
| 4,445,894 | 5/1984 | Kovacs | 128/DIG. 26 X |
| 4,453,933 | 6/1984 | Speaker. | |
| 4,569,348 | 2/1986 | Hasslinger | 128/DIG. 15 X |
| 4,591,356 | 5/1986 | Christie | 604/179 |
| 4,605,397 | 8/1986 | Ligon et al. | |
| 4,665,566 | 5/1987 | Garrow | 128/DIG. 15 X |
| 4,738,662 | 4/1988 | Kalt et al. | 128/DIG. 26 X |
| 4,795,429 | 1/1989 | Feldstein. | |
| 4,905,714 | 3/1990 | Drennen | 128/DIG. 15 X |
| 4,988,062 | 1/1991 | London. | |
| 5,082,111 | 1/1992 | Corbitt, Jr. et al. | 128/DIG. 15 X |
| 5,205,832 | 4/1993 | Tuman | 604/179 |
| 5,263,941 | 11/1993 | Cockrill. | |
| 5,334,186 | 8/1994 | Alexander. | |
| 5,496,282 | 3/1996 | Militzer et al. | 604/179 |

*Primary Examiner*—Sam Rimell
*Attorney, Agent, or Firm*—Chernoff, Vilhauer, McClung & Stenzel

[57] ABSTRACT

A management system for flexible lines, such as tubes and cables, used in the medical treatment of a patient includes a flexible expanse of material and a plurality of separate connectors mounted at different positions on the material. The connectors are separately operable for attaching and detaching respective lines independently of the attachment and detachment of other lines. Each of the connectors is preferably detachably mountable upon the material alternatively in different positions and orientations to accommodate the random positioning and orientation of the lines. The expanse of material lies supportably atop the body of the patient and can be selectively detachably separated into two line-connecting parts to quickly enable access to the patient's chest and abdominal areas for treatment. The expanse of material adjustably fastens selectively to patient reclining supports of different types such as stretchers and beds to facilitate transfer of the patient.

16 Claims, 2 Drawing Sheets

5,624,403

MANAGEMENT SYSTEM FOR MEDICAL TUBES AND CABLES

BACKGROUND OF THE INVENTION

This invention relates to improvements in systems for managing flexible lines, such as tubes and cables, used in the medical treatment of a patient. The invention is particularly useful for critical patients to whom are attached numerous tubes for the infusion and withdrawal of fluids and electrical cables for monitoring the patient's condition. Typical lines of this type include IV tubes, suction tubes, drainage tubes, catheters, ventilator tubes, blood pressure, heart and oxygen monitor cables, and the like.

The majority of such tubes and cables are at least about six to eight feet in length and extend to the patient from their respective sources positioned on both sides of the patient. Even if the patient is not being transported, it is common for the patient to become entangled in the tubes and cables, risking injury or disconnection. The risk is much higher in the emergency situation where the patient must be transported by an ambulance or aircraft to a hospital emergency room where the patient is transferred from a stretcher or sled to a bed, and then further transferred to other locations such as an intensive care unit or operating room, depending upon the treatment required. Under such circumstances, stabilization and unitization of the tubes and cables is needed so that their positions relative to the patient are controlled despite the transporting and transferring activities.

Moreover, it is important that the tubes and cables be easily and quickly attachable and detachable independently of each other at random positions and orientations relative to the patient, and be easily identifiable as to their respective functions so that no tube or cable is erroneously connected or disconnected.

In addition, the tube and cable management system should be reliably stabilized relative to the patients' reclining support, such as a sled, stretcher, gurney, bed or the like, regardless of the type of reclining support used, so that the management system remains in proper position despite movement of the patient on the support device. When the patient is transferred from one reclining support to another, the management system should automatically remain in proper position relative to the patient throughout the transfer process. Nevertheless, the attachment structure should not prevent access by medical personnel to any portion of the patient's body.

SUMMARY OF THE PRESENT INVENTION

The present invention satisfies all of the foregoing needs in a mutually compatible manner by providing a flexible expanse of material which can be placed closely adjacent to the patient and which has connectors for selectively connecting flexible medical lines, such as tubes and cables, to the expanse of material.

According to one aspect of the invention, the expanse of material has a plurality of separate connectors mounted at different positions thereon, each including separately operable means for selectively attaching and detaching a respective line independently of the attachment and detachment of other lines.

According to a separate aspect of the invention, each of the connectors is detachably mountable on the expanse of material alternatively in different positions and orientations to accommodate quick and easy random positioning of the lines.

According to a further separate aspect of the invention, the expanse of material is mountable supportably atop the body of the patient so that it will automatically retain the lines in proper position relative to the patient as the patient is transferred from one reclining support to another. The expanse of material is detachably separable into two separate parts to enable quick access to the patient's chest and abdominal areas if necessary, despite its placement atop the patient's body.

According to another separate aspect of the invention, the expanse of material, while atop the body of the patient, is capable of being fastened, on both sides of the patient, adjustably to different types of reclining supports such as sleds, stretchers, gurneys and beds so that its position is maintained despite the patient's movement on the reclining support.

According to yet another separate aspect of the invention, the line connectors on the expanse of material are of different colors, and a plurality of markers of the same different colors are also provided for attachment to corresponding ones of the lines at locations remote from the expanse of material so that the position of each line adjacent to the patient can be quickly associated with its respective source and thereby identified as to its function.

The foregoing and other objectives, features and advantages of the present invention will be more readily understood upon consideration of the following detailed description of the invention taken in conjunction with the accompanying drawings.

DETAILED DESCRIPTION OF THE PREFERRED EMBODIMENT

Figure 1:
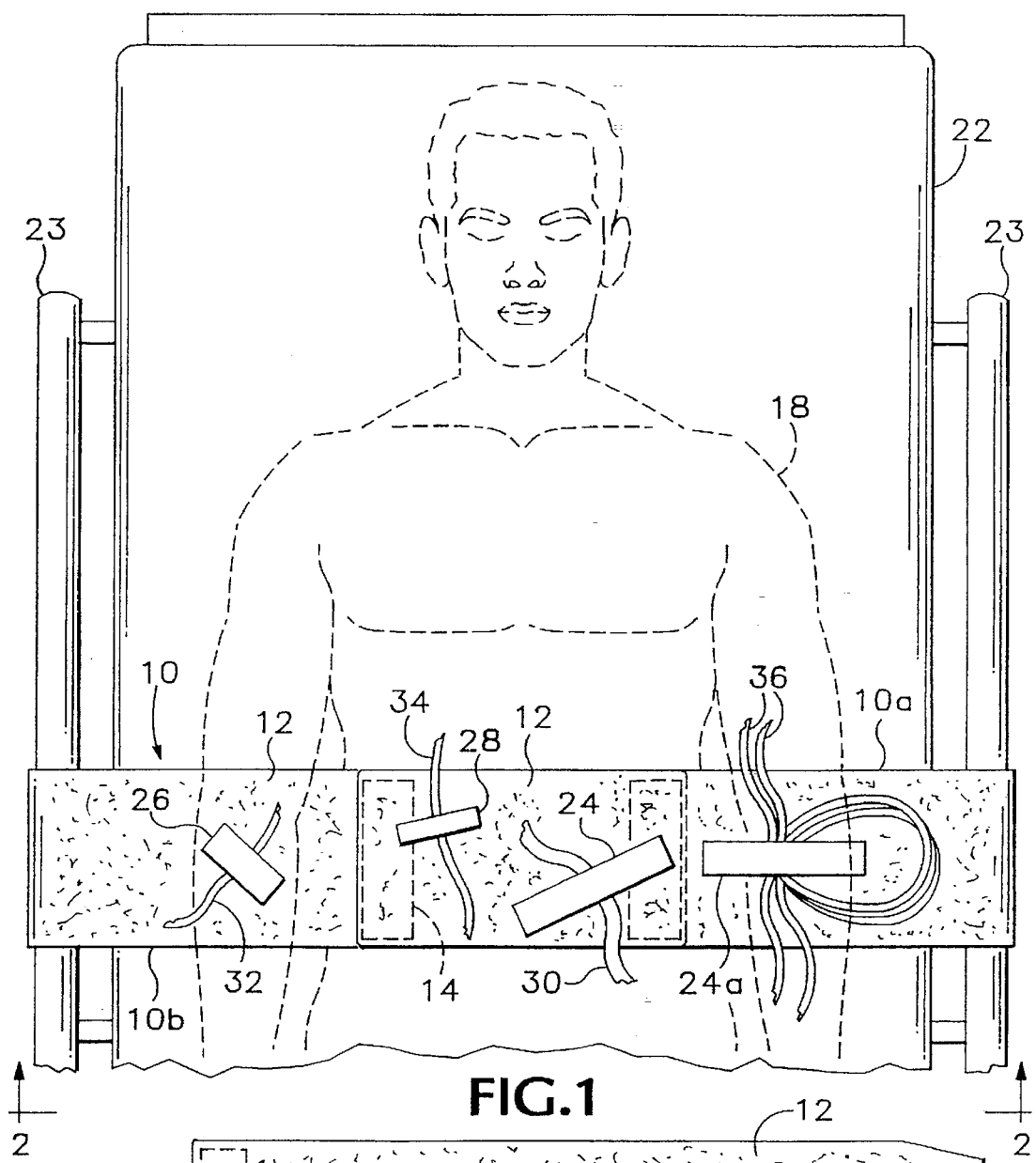
FIG. 1 is a top view of an exemplary embodiment of the invention.
Figure 3:
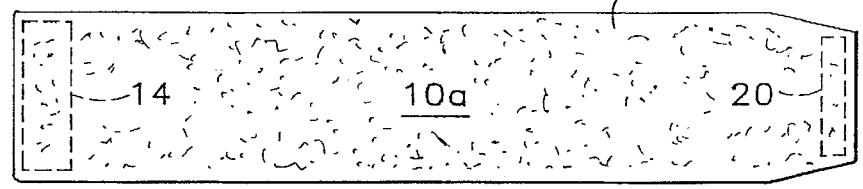
FIGS. 3 and 4 are top views of respective separable parts of the exemplary embodiment of FIG. 1.
Figure 4:
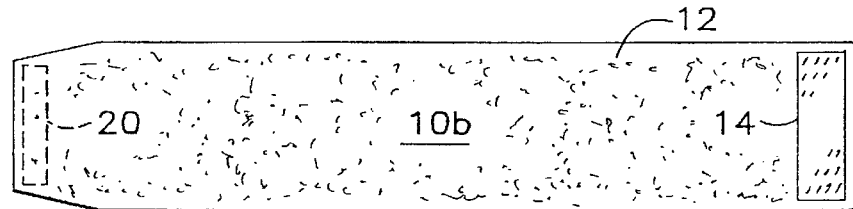

An exemplary embodiment of the present invention comprises an elongate, flexible expanse of material, indicated generally as 10, having an upwardly-facing surface 12 preferably composed of loop pile material marketed under the trademark VELCRO. Preferably, the expanse 10 comprises two separate parts, 10a and 10b, detachably interconnected with each other by at least one piece 14 of VELCRO™ hook material permanently attached beneath part 10a and detachably engaging the loop pile upper surface 12 of part 10b. Although not critical, it is preferable that the parts 10a and 10b also have a downwardly-facing VELCRO™ loop pile surface 16 beneath the upper surface 12, attached by adhesion or stitching to the surface 12. An intermediate non-absorbent foam layer (not shown) may be inserted between the surfaces 12 and 16 for cushioning purposes. A further VELCRO™ hook piece 14 may be permanently attached to the upper surface 12 of the part 10b for detachably engaging the downwardly facing lower loop pile surface 16 of part 10a. The resultant overlapping detachable interconnection of the parts 10a and 10b provides not only easy detachment of the two parts from each other, but also length adjustment of the expanse 10, for reasons to be explained hereafter. Alternatively, it is within the scope of the present invention to provide the expanse 10 as a single inseparable piece or, if detachable into two parts, without such a centrally-located length adjustment feature.

The outer ends of each part 10a, 10b include further VELCRO™ hook pieces 20 permanently connected to surface 16 for detachably engaging the surface 16 and thereby forming end loops 21 for fastening the expanse of material 10, on both sides of the patient 18, to rails 23 or other suitable portions of a patient reclining support 22 while the expanse 10 is supported atop the body of the patient 18. If the expanse 10 happens to be inverted from its orientation shown in the drawings, the loops 21 can engage the rails 23 by passing under and over, rather than over and under, the rails. Alternatively, hook pieces 20 could be permanently attached to both surfaces 12 and 16 so that the loops 21 could be passed around the rails 23 selectively in either direction. Preferably, however, the loops 21 pass over and under the rails as shown in the drawings to maximize the exposed area of the upwardly-facing surface 12.

To accommodate the transfer of the patient between different types of reclining supports having rails or other anchoring points at different heights, the above-described length adjustment structure at the middle of the expanse 10 and/or the size of the loops 21 formed by the hook pieces 20 can be adjusted to ensure that the expanse 10 lies loosely atop the patient but without excessive slack which might permit too much movement of the expanse 10 if the patient moves or is moved.

Detachably mountable to whichever surface 12 or 16 is facing upwardly are a plurality of separate connectors 24, 26, 28 comprising VELCRO™ hook strips, preferably of different sizes and colors. The hook surfaces may be located on one side or both sides of the strips. Each of the connectors 24, 26, 28 is detachably mountable upon the expanse 10 selectively in any of multiple different positions and orientations as exemplified by FIG. 1 so as to attach respective lines such as 30, 32, 34 to the expanse 10 in any randomly selected positions and orientations. Each connector 24, 26, 28 is separately operable to attach or detach a respective line with respect to the expanse 10 independently of the attachment or detachment of any other line so that the manipulation of one line need not disturb the other lines. Although the connectors 24, 26 and 28 are preferably completely detachable from the expanse 10 to maximize their versatility with respect to positioning and orientation, it is within the scope of the present invention that the connectors 24, 26, 28 could be permanently attached (for example, by stitching at one end) to the expanse 10. This would detract from the above-described positioning versatility, but would nevertheless still permit independent attachment and detachment of each line with respect to the expanse 10.

Figure 5:
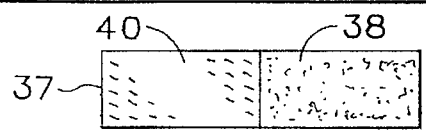
FIG. 5 is an enlarged top view of an exemplary line marker used in the embodiment of FIG. 1.
Figure 2:
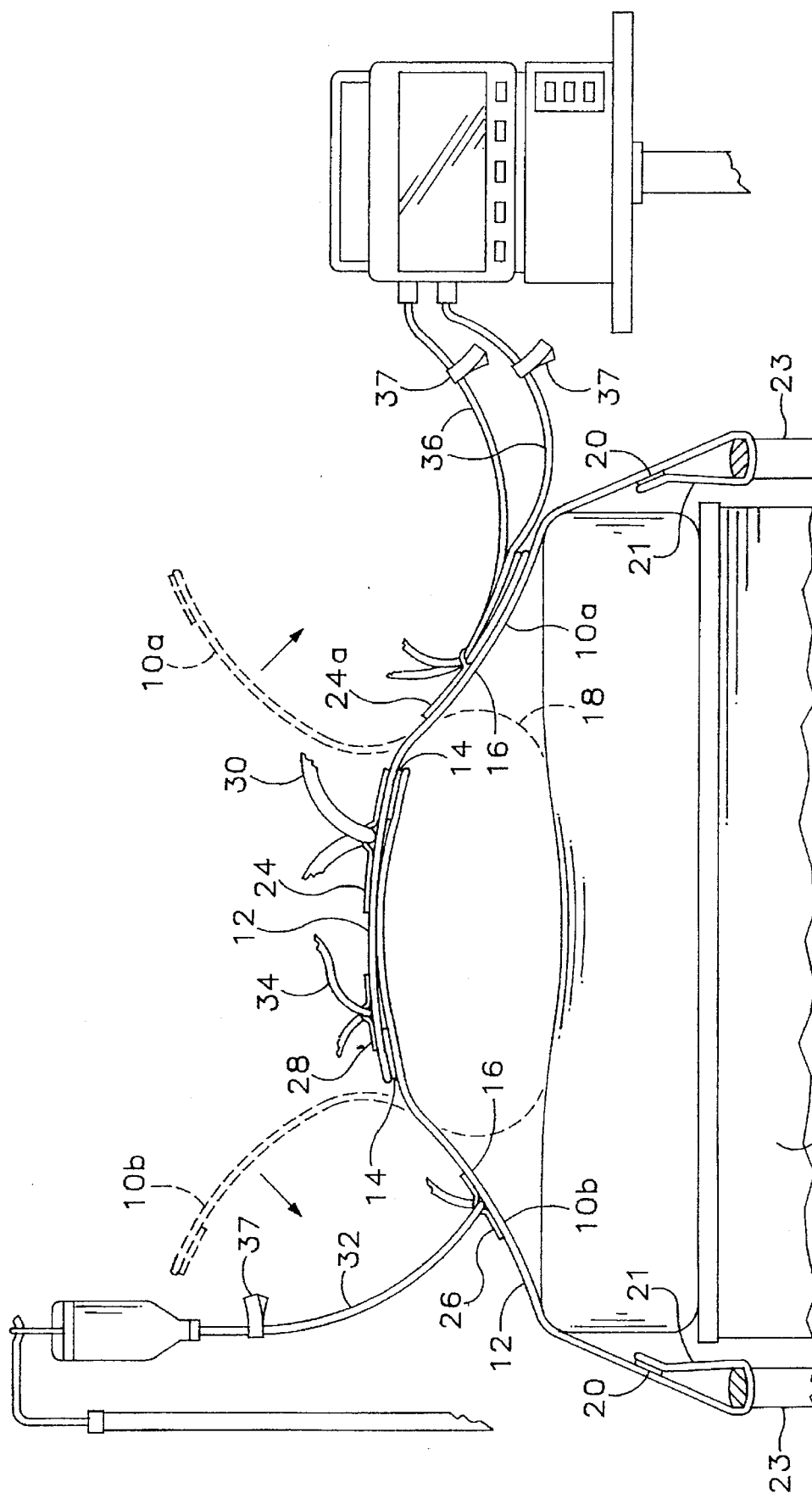
FIG. 2 is an end view taken along line 2—2 of FIG. 1.

Preferably, respective markers 37 of different colors corresponding to the different colors of the connectors 24, 26, 28 are provided for connection to respective ones of the lines 30, 32, 34 at locations remote from the expanse 10 as shown in FIG. 2 to identify each connector and its related line with the respective source of the line. Each marker may, for example, have both a VELCRO™ loop pile surface 38 and hook surface 40 as shown in FIG. 5 which, when folded together around a line, quickly connect the marker detachably to the line. Alternatively, the markers 37 could be made of other easily-connectable colored materials, such as adhesive tags.

The respective different sizes of the connectors 24, 26, 28 enable the connectors conveniently to attach lines of different sizes to the expanse 10. For example, a larger connector such as 24 or 24a would normally be used for a thicker, heavier line such as 30, or for lines such as 36 which need to be coiled within the connector to take up excess slack. Smaller connectors, on the other hand, such as 26 or 28 would be used for correspondingly thinner, lighter lines.

Although VELCRO™ loop and hook material is preferable for all of the above-described different attachment/detachment functions employed in the present invention, it is also within the scope of the invention to use other types of quickly operable attachment/detachment structures for any or all of such functions, such as snaps, buttons, toggles, hooks, rings, eyelets, clamps, clasps or the like.

In use, the expanse 10 is laid transversely atop the patient with the side 12 facing upwardly, and connected by the end loops 21 to the rails 23 or other suitable side connection points of the reclining support 22. Length adjustment of the expanse 10 for a proper fit can be accomplished by varying the overlap of the parts 10a and 10b where they are joined in the middle of the expanse 10, and/or by varying the size of the end loops 21. The various lines 30, 32, 34, 36 may be applied to the patient either before or after the expanse 10 has been placed atop the patient. With the expanse in place, each line is attached separately to the expanse 10 by a respective connector such as 24, 26, 28, and corresponding colored markers 37 are connected to each line in a location adjacent its respective source and remote from the expanse 10. Lines emanating from sources located on the right side of the patient are connected to the part 10a or 10b of the expanse 10 which is also located on the patient's right side, while lines emanating from sources on the patient's left side are connected to the opposite part of the expanse 10. If the patient is to be transferred from one reclining support to another, the loops 21 are disconnected and the patient is transferred while the expanse 10 remains supported atop the patient's body. If it is necessary to gain access to the patient's chest or abdomen, the parts 10a and 10b are quickly detached from each other and folded to the sides as shown in phantom in FIG. 2, while the respective right- and left-hand lines remain connected to the respective parts 10a and 10b. In this way, lines emanating from each side of the patient remain on their respective side and do not cross over the patient when the parts 10a and 10b are separated.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A management system for flexible lines, such as tubes and cables, used in the medical treatment of a patient, said system comprising;
    (a) an elongate flexible member having opposite ends and including a flexible expanse of material;
    (b) a plurality of separate connectors mounted at different positions on said expanse of material;
    (c) each of said connectors including separately operable means for selectively attaching and detaching a respective one of said lines with respect to said expanse of material independently of the attachment and detachment of other ones of said lines;
    (d) a patient reclining support having a torso-supporting portion;
    (e) said elongate flexible member including, adjacent said opposite ends, respective fasteners detachably fastened to said patient reclining support at respective fastening locations on said support on opposite sides of said torso-supporting portion of said support, said elongate flexible member having means for adjusting the length thereof between said respective locations when lying atop the torso of a patient to enable said fasteners to operably engage different types of patient reclining supports having substantial differences with respect to said locations.

2. The system of claim 1 wherein each of said connectors is detachably mountable on said expanse of material.

3. The system of claim 1 wherein each of said connectors is detachably mountable selectively in different orientations on said expanse of material.

4. The system of claim 1 wherein each of said connectors is detachably mountable selectively at different positions on said expanse of material.

5. The system of claim 1 wherein said expanse of material includes two separate parts of said material each having at least one of said connectors mounted thereon, said separate parts being selectively completely detachable and reattachable with respect to each other at a location longitudinally between said fasteners to selectively expose or cover said torso.

6. The system of claim 1 wherein respective ones of said connectors are of different colors, further including a plurality of markers of said different colors having means for selectively connecting said markers separately to respective ones of said lines at locations remote from said expanse of material.

7. The system of claim 1 wherein each of said connectors comprises a piece of flexible material smaller than said expanse of material.

8. The system of claim 1 wherein said connectors are of different sizes in relation to each other to attach lines of different sizes to said expanse of material.

9. A management system for flexible lines, such as tubes and cables, used in the medical treatment of a patient, said system comprising:
(a) an elongate flexible member having opposite ends and including a flexible expanse of material;
(b) a plurality of separate connectors for said lines;
(c) cooperative means on said expanse of material and said connectors for detachably mounting each of said connectors upon said expanse of material selectively in any of multiple different positions and orientations;
(d) a patient reclining support having a torso-supporting portion;
said elongate flexible member including, adjacent said opposite ends, respective fasteners detachably fastener to said patient reclining support at respective fastening locations on said support on opposite sides of said torso-supporting portion of said support, said elongate flexible member having means for adjusting the length thereof between said respective locations when lying atop the torso of a patient to enable said fasteners to operably engage different types of patient reclining supports having substantial differences with respect to said locations.

10. The system of claim 9 wherein said expanse of material includes two separate parts of said material each having at least one of said connectors mounted thereon, said separate parts being selectively completely detachable and reattachable with respect to each other at a location longitudinally between said fasteners to selectively expose or cover said torso.

11. The system of claim 9 wherein respective ones of said connectors are of different colors, further including a plurality of markers of said different colors having means for selectively connecting said markers separately to respective ones of said lines at locations remote from said expanse of material.

12. The system of claim 9 wherein each of said connectors comprises a piece of flexible material smaller than said expanse of material.

13. The system of claim 9 wherein said connectors are of different sizes in relation to each other to attach lines of different sizes to said expanse of material.

14. A management system for flexible lines, such as tubes and cables, used in the medical treatment of a patient, said system comprising:
(a) a flexible expanse of material having means for selectively connecting said lines to said expanse;
(b) said expanse of material including means for mounting said expanse supportably atop the torso of said patient and including two separate parts of said expanse each capable of connecting a respective one of said lines to said expanse, said separate parts being selectively completely detachable and reattachable with respect to each other to selectively expose or cover said torso;
(c) a patient reclining support having a torso-supporting portion;
(d) said separate parts of said expanse having respective fasteners detachably fastened to said patient reclining support at respective fastening locations on said support on opposite sides of said torso, supporting portion of said support.

15. A management system for flexible lines, such as tubes and cables, used in the medical treatment of a patient, said system comprising:
(a) an elongate flexible member having opposite ends and including a flexible expanse of material having means for selectively connecting said lines to said expanse;
(b) said elongate flexible member including means for mounting said expanse supportably atop the torso of said patient;
(c) a patient reclining support having a torso-supporting portion;
(d) said elongate flexible member including, adjacent said opposite ends, respective fasteners detachably fastened to said patient reclining support at respective fastening locations on said support on opposite sides of said torso-supporting portion of said support, said elongate flexible member having means for adjusting the length thereof between said respective locations when lying atop the torso of a patient to enable said fasteners to operably engage different types of patient reclining supports having substantial differences with respect to said locations.

16. A management system for flexible lines, such as tubes and cables, used in the medical treatment of a patient, said system comprising:
(a) a flexible expanse of material:
(b) a plurality of separate connectors for said lines mounted at different positions on said expanse of material, said connectors being of different colors;
(c) a plurality of markers of said different colors having means for selectively connecting said markers separately to respective ones of said lines at locations remote from said expanse of material;
(d) a patient reclining support having a torso-supporting portion;
(e) said flexible expanse having respective fasteners detachably fastened to said patient reclining support at respective fastening locations on said support on opposite sides of said torso-supporting portion of said support.

* * * * *

UNITED STATES PATENT AND TRADEMARK OFFICE
CERTIFICATE OF CORRECTION

PATENT NO. : 5,624,403

DATED : April 29, 1997

INVENTOR(S) : Jerrie L. Jaquith

It is certified that error appears in the above-indentified patent and that said Letters Patent is hereby corrected as shown below:

Col. 5, line 45, Insert --(e)-- before "said"

Col. 6, line 25, Delete "," (comma) between "torso" and "supporting" and substitute therefor a hyphen.

Signed and Sealed this

Seventeenth Day of August, 1999

Attest:

Q. TODD DICKINSON

Attesting Officer

Acting Commissioner of Patents and Trademarks